(12) United States Patent
Nelson et al.

(10) Patent No.: US 10,792,149 B2
(45) Date of Patent: Oct. 6, 2020

(54) EXPANDABLE STENT AND METHODS OF CRIMPING AND EXPANDING SUCH STENT

(71) Applicant: Strait Access Technologies Holdings (Pty) Ltd, Observatory (ZA)

(72) Inventors: Grant Leigh Nelson, Auckland (NZ); Kenneth Stuart Park, Newlands (ZA); Braden Sydney Clive Van Breda, Newlands (ZA); Deon Bezuidenhout, Cape Town (ZA); Peter Zilla, Cape Town (ZA); Harish Appa, Cape Town (ZA)

(73) Assignee: Strait Access Technologies Holdings (Pty) Ltd (ZA)

( * ) Notice: Subject to any disclaimer, the term of this patent is extended or adjusted under 35 U.S.C. 154(b) by 123 days.

(21) Appl. No.: 16/086,480

(22) PCT Filed: Apr. 26, 2017

(86) PCT No.: PCT/ZA2017/050025
§ 371 (c)(1),
(2) Date: Sep. 19, 2018

(87) PCT Pub. No.: WO2017/190161
PCT Pub. Date: Nov. 2, 2017

(65) Prior Publication Data
US 2019/0099266 A1    Apr. 4, 2019

(30) Foreign Application Priority Data
Apr. 27, 2016  (GB) .................................. 1607351.2

(51) Int. Cl.
*A61F 2/24* (2006.01)
*A61F 2/86* (2013.01)

(52) U.S. Cl.
CPC .......... *A61F 2/2418* (2013.01); *A61F 2/2415* (2013.01); *A61F 2/2427* (2013.01);
(Continued)

(58) Field of Classification Search
CPC ........ A61F 2/2418; A61F 2/86; A61F 2/2463; A61F 2/2409; A61F 2/82; A61F 2/844; A61F 2/89; A61F 2/90; A61F 2002/825
See application file for complete search history.

(56) References Cited

U.S. PATENT DOCUMENTS

| 7,258,697 B1 * | 8/2007 | Cox .......................... A61F 2/91 623/1.14 |
| 8,216,301 B2 | 7/2012 | Bonhoeffer et al. |
| 8,992,608 B2 | 3/2015 | Haug et al. |

FOREIGN PATENT DOCUMENTS

| GB | 2513195 A | 10/2014 |
| WO | 0064355 A1 | 11/2000 |

(Continued)

OTHER PUBLICATIONS

Search Report and Written Opinion in International Patent Application, Application No. PCT/ZA2017/050025, dated Sep. 28, 2017.

*Primary Examiner* — Brian A Dukert
*Assistant Examiner* — Amanda M Barkan
(74) *Attorney, Agent, or Firm* — Haugen Law Firm PLLP

(57) ABSTRACT

An expandable stent comprises a cylindrical wall made up of lattice members connected to each other, at least one first arm and at least one second arm. The first arm comprises: a first non-linear member that is connected at each of its axial ends to a lattice member at respective first junctions; a second non-linear member connected at each axial end to a lattice member; and at least one bridge member extending between the first member and the second member. The second arm comprises: a first non-linear member that is (Continued)

connected at each of its axial ends to a lattice member; a second non-linear member connected at each axial end to a lattice member; and at least one bridge member extending between the first member and the second member. The second member of the first arm is generally U-shaped, extending from its axial ends towards: (i) a first axial end of the stent; and (ii) towards the bridge of the first arm. The second member of the second arm is generally U-shaped, extending from its axial ends towards: (i) a first axial end of the stent; and (ii) towards the bridge of the second arm. The first arm is disposed at a second axial end of the stent, and the second arm is: (i) axially spaced from the first arm towards the first axial end of the stent; and (ii) axially aligned with the first arm. Furthermore, the first member and the second member of each of the first and second arms are connected to lattice members at their axial ends only. Upon radial expansion of the stent from a radially crimped condition under the influence of an external force, tension in: (i) the bridge of the first arm; and (ii) the bridge member of the second arm, causes the second members of both the first and second arms to protrude radially outwards, respectively.

16 Claims, 10 Drawing Sheets

(52) U.S. Cl.
CPC ......... *A61F 2/86* (2013.01); *A61F 2220/0008* (2013.01); *A61F 2220/0025* (2013.01)

(56) References Cited

FOREIGN PATENT DOCUMENTS

| | | |
|---|---|---|
| WO | 2011002996 A2 | 1/2011 |
| WO | 2011104269 A1 | 9/2011 |
| WO | 2015061021 A1 | 4/2015 |

* cited by examiner

EXPANDABLE STENT AND METHODS OF CRIMPING AND EXPANDING SUCH STENT

BACKGROUND

The present invention relates to an expandable stent and methods of crimping and expanding such stent. More particularly, the present invention relates to an expandable cylindrical stent with axially spaced arms that extend axially in the same direction, which stent can plastically be deformed to a crimped condition, and which crimped stent can be expanded radially with the aid of a dilatation device to cause the axially spaced arms to protrude radially beyond the radial wall of the stent.

In the recent years, there has been a big movement towards minimally invasive surgeries, which has led to substantial development in the field of vascular devices, particularly vascular stents and trans-catheter heart valves. This is mainly as a result of the reduced surgical time, risks and recovery time as well as hospitalisation time of the patients involved with minimally invasive treatments.

The main aims of vascular stents and trans-catheter heart valves are to reinforce vessel walls and to restore blood flow to normal physiological conditions. Vascular stents are used to open up an obstructed vessel. Similarly trans-catheter valves, which consist of a stent frame and flexible leaflets, are used to replace non-functioning valves such that appropriate blood flow is restored with better opening and closing of the valve.

Minimally invasive procedures are most commonly performed using an endovascular procedure, where a small incision is made to have access to a blood vessel to reach a desired position. The access point depends on the area to which the device is required. To reach the desired location a guide wire is used to guide the device. The decision of the access point also relies on the patient's medical condition; for example, for a heart valve a trans-femoral (through the femoral artery), trans-apical (through the apex of the heart), or a sub-clavian (through the sub-clavian artery) approach may be used. For the trans-apical approach or sub-clavian approach a mini-thoracotomy is required to access the heart.

These procedures require that the valve or stent is compressed to a small diameter prior to insertion into the body such that it can either navigate through the vascular system or be small enough that only a small incision is required. With the help of a guide wire and sophisticated imaging techniques such as echocardiography and/or fluoroscopy or other methods the compressed device is placed in the desired position. Once satisfactory positioning is achieved the device is expanded to the appropriate diameter.

There are two ways to expand the valve/stent to the final desired diameter either by using a dilatation device (e.g. a balloon) or by allowing it to self-expand. For the balloon expandable method stainless steel or nickel-cobalt-chromium alloys are widely used for stents and valves. Initially the stent is compressed from a larger to a smaller diameter. Due to the material property of the alloys and stent designs used, the stent is plastically deformed and stays in a compressed state. The stent is then expanded to its final opened state with the aid of a balloon or a mechanical system.

Self-expandable stents use a different method; they exploit the characteristic superelastic and shape memory properties of nitinol, a nickel-titanium alloy. The material can be given a shape memory using appropriate heat treatments. Here the stent is given the memory of the shape of an expanded state. For the minimally invasive procedure the stent is compressed and covered with a sheath (that confines it to its crimped state which is then removed when the correct position is reached allowing the stent to expand to its opened shape).

Once the stent is expanded it has to stay in position. Anchoring of the device is crucial for proper function and to avoid embolization or migration, which can be fatal. For minimally invasive procedures anchoring is achieved by either using friction or structures that stay in cavities to prevent motion or harpoon/hook-like elements that anchor in the surrounding vessel.

With its shape memory advantage, nitinol stents can be designed to have complex shapes or configurations when expanded. That allows nitinol based stents to anchor adequately in a vessel. However, nitinol stents have a few disadvantages. The diameter of stents designed with nitinol cannot be readily adjusted, which makes sizing critical. There are risks of both oversizing and undersizing, which could lead to valve leakage and/or migration. When oversized the typical continuous high forces of nitinol based stents can sometimes lead to trauma. In the case of trans-catheter valves, continuous contact force between the stent and the heart may lead to compression of the electrical conduction structures in the heart, which in turn may necessitate the implantation of a permanent pacemaker. In addition, nitinol stents require a restraining sheath once in a compressed condition to prevent the stent from expanding at a time when expansion is not desired. These sheaths require more complex delivery systems to allow operators to control the unsheathing operation. Furthermore, the relatively lower strength of nitinol stents means that post-expansion of the stent using another balloon may be required to ensure that the stent is sufficiently opposed the wall of the lumen or body cavity to reduce the likelihood of blood flow around the outside of the stent.

On the other hand, balloon expandable stents have been designed to expand generally in a cylindrical configuration. An advantage of balloon-expandable stents is that they ensure a rigid circular structure due to the high radial strength of the material and work hardening undergone during the crimping process. With a balloon deployment, post dilatation of stent is seldom used. Standard cylindrical balloon-expandable stents rely on friction between the stent and the body to prevent migration. In the case of commercially available balloon-expandable trans-catheter valve stents it is well known that calcium must be present in the valve annulus to provide a secure base for anchorage, and that valves readily migrate or embolize if the rigidity provided by the calcium is not present.

With the above in mind it can be seen that anchoring for both balloon-expandable and nitinol stents need to be improved. However with the added benefits of balloon expandable stents, anchoring mechanisms, arms or non-cylindrical stent behaviour would be additionally beneficial to improving the device behaviour in situ.

Various forms of deformable stents exist. For example:
WO00/64355 "Intravascular folded tubular endoprosthesis" describes an expandable stent with radially protruding barbs. A drawback of this stent is that the barbs protrude even when the stent is in a radially compressed state.
GB2513195 "A stent for a prosthetic heart valve" describes an expandable stent with arms, which arms are caused to protrude radially by tethers that form part of the valve deployment device. A drawback of this device is that deployment of the arms is complex, requiring a custom dilatation device.

U.S. Pat. No. 8,992,608 "Everting heart valve" describes an expandable stent including arms that are caused to protrude radially upon axial compression of the stent. A drawback of this device is that deployment of the arms requires axial compression of the stent and a custom dilatation device.

U.S. Pat. No. 8,216,301 "Implant implantation unit" describes an expandable stent and arms that protrude from the outer radial wall of the stent and resiliently pivot radially outwards from the stent. A drawback of this device is that the arms must be restrained from pivoting radially outwards during insertion of the device into a patient.

WO2011/002996 "Apparatus and method for replacing a diseased cardiac valve" describes an expandable stent wherein radial expansion of the stent causes opposed arms to protrude radially to capture a structure on a vessel wall between the opposed arms. A drawback of this device is that the degree to which the arms protrude radially from the stent wall must accurately be determined to ensure proper engagement of the arms and the formation on the vessel. Should the arms not protrude sufficiently radially properly to engage the structure on the vessel wall, slippage of the stent along the vessel may cause the structure on the vessel to pass beyond the arm, unable again properly to become engaged by the stent.

It is an object of the present invention to address the above drawbacks and to provide an expandable stent wherein:
(i) the arms form an integral part of the cylindrical wall of the stent;
(ii) radial expansion of the stent causes the arms to protrude radially;
(iii) the stent can be expanded and the arms caused to protrude without requiring a customised dilatator; and
(iv) the stent includes at least two axially spaced and axially aligned arms that extend radially from the stent wall by different degrees, such that, should the stent shift axially along the vessel, a structure on the vessel wall that bypasses a first arm may properly be engaged by a second arm that is axially spaced from, and axially aligned with the first arm. This is particularly relevant when the first and second arms are required to rest on the same valve leaflet free edge.

SUMMARY OF THE INVENTION

According to a first aspect of the invention, there is provided an expandable stent that comprises a cylindrical wall made up of:
lattice members connected to each other;
at least one first arm that comprises:
  a first non-linear member that is connected at each of its axial ends to a lattice member at respective first junctions; and
  a second non-linear member connected at each axial end to: (i) a lattice member; or (ii) the first member of the first arm; and
  at least one bridge member extending between the first member and the second member,
at least one second arm that comprises:
  a first non-linear member that is connected at each of its axial ends to a lattice member; and
  a second non-linear member connected at each axial end to a lattice member; and
  at least one bridge member extending between the first member and the second member, characterised in that:
  the second member of the first arm is generally U-shaped, extending from its axial ends towards: (i) a first axial end of the stent; and (ii) towards the bridge of the first arm;
  the second member of the second arm is generally U-shaped, extending from its axial ends towards: (i) a first axial end of the stent; and (ii) towards the bridge of the second arm;
  the first arm is disposed at a second axial end of the stent, and the second arm is: (i) axially spaced from the first arm towards the first axial end of the stent; and (H) axially aligned with the first arm; and
  the first member and the second member of each of the first and second arms are connected to lattice members at their axial ends only,
such that, upon radial expansion of the stent from a radially crimped condition under the influence of an external force, tension in: (i) the bridge of the first arm; and (ii) the bridge member of the second arm, causes the second members of both the first and second arms to protrude radially outwards, respectively.

Typically, the length of the first member of the first arm is longer than the length of the first member of the second arm.

Generally, the circumferential spacing between the axial ends of the second member of the first arm is greater than the circumferential spacing between the axial ends of the second member of the second arm.

Preferably, the first member of the first arm defines a stiffened portion at each axial end of such first member, which stiffened portions are spaced from each other to define a deformable portion therebetween.

Typically, the first member of the first arm is substantially M-shaped, defining a pair of leg portions with a curved portion therebetween, wherein each leg portion comprises a stiffened portion and the curved portion comprises the deformable portion.

Generally, the stent includes: (i) three first arms that are circumferentially equi-offset from each other; and (ii) three second arms that are circumferentially equi-offset from each other.

Preferably, in respect of each second arm, the axial ends of the first member of the second arm are spaced from the axial ends of the second member of the second arm, with at least a portion of a lattice member extending therebetween.

Typically, the circumferential spacing between the axial ends of the first member of each first arm is greater than the circumferential spacing between the axial ends of the first member of each second arm.

Generally, the first member of each second arm is generally U-shaped.

Preferably, in respect of each first arm:
  each stiffened portion of the first member of the first arm is at least 1.3 mm in length; and
  the stiffened portions of the first member of the first arm on the one hand and the second member of the first arm on the other hand are disposed on opposite sides of a virtual plane that: (i) extends between the respective first junctions; and (ii) is transverse the longitudinal axis of the stent,
such that, upon radial expansion of the stent from a radially crimped condition under the influence of an external force, tension in the lattice members at the first junctions causes rotation of the stiffened portions of the first member of the first arm at the first junctions, thereby causing the ends of the stiffened portions distal the second member of the first arm to rotate towards each other.

Typically, the stent is right circular cylindrical in shape.

Generally, the stent further includes valve leaflets: (i) located within the stent; and (ii) secured to lattice members.

Preferably: (i) three contiguous lattice members are arcuate in shape; (ii) each arcuate-shaped lattice member extends along at least 25% of the perimeter of the stent; (iii) each arcuate-shaped lattice member defines a series of apertures or rings along its length; and (iv) the valve leaflets are sutured to such arcuate shaped lattice members via such apertures or rings.

According to a second aspect of the invention, there is provided a method of crimping a stent according to the first aspect of the invention, which method includes the steps of:
  causing primary deformation of the lattice members that induces: (i) relative angular displacement of the lattice members at their points of connection to each other and general deformation of lattice members to a collapsed state; and (ii) adjacent first members of adjacent first arms to contact each other; and
  causing secondary deformation of the lattice members wherein further compression of the collapsed lattice members causes the stiffened portions of the first members of each first arm plastically to deform.

Typically, the method further includes the step of pinching adjacent stiffened portions of adjacent first members of adjacent first arms together, thereby causing such stiffened portions further to deform plastically.

According to a third aspect of the invention, there is provided a method of expanding a stent according to the first aspect of the invention, which method includes the steps of:
  positioning the stent that has previously been crimped through a heart valve with the first arms and the second arms extending past the free ends of the valve leaflets;
  expanding a dilatation device within the stent to cause: (i) the stent to expand; and (ii) the first and second arms to protrude radially relative to the adjacent lattice members; and
  displacing the stent axially relative to the valve to cause the first arms or the second arms to rest on the free ends of the valve leaflets, with the free ends of the resting first arms or second arms spaced from the intersection of the valve leaflets and aortic root.

BRIEF DESCRIPTION OF THE DRAWINGS

The invention will now be described in more detail, by way of examples only, with reference to the accompanying drawings in which.

DESCRIPTION OF THE INVENTION

Figure 1:
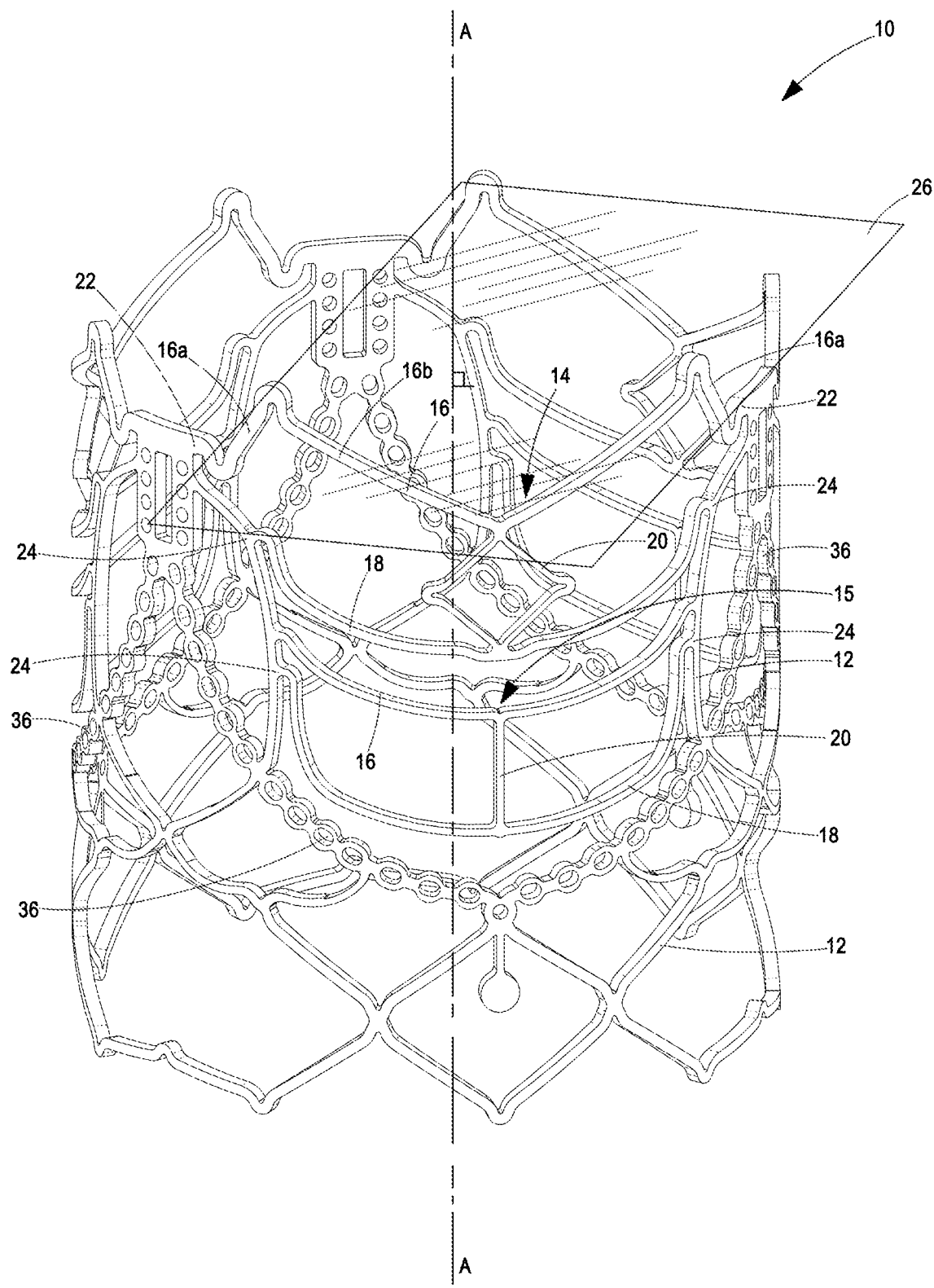
FIG. 1 is a perspective view of an expandable cylindrical stent according to a preferred embodiment of a first aspect of the invention.
Figure 2:
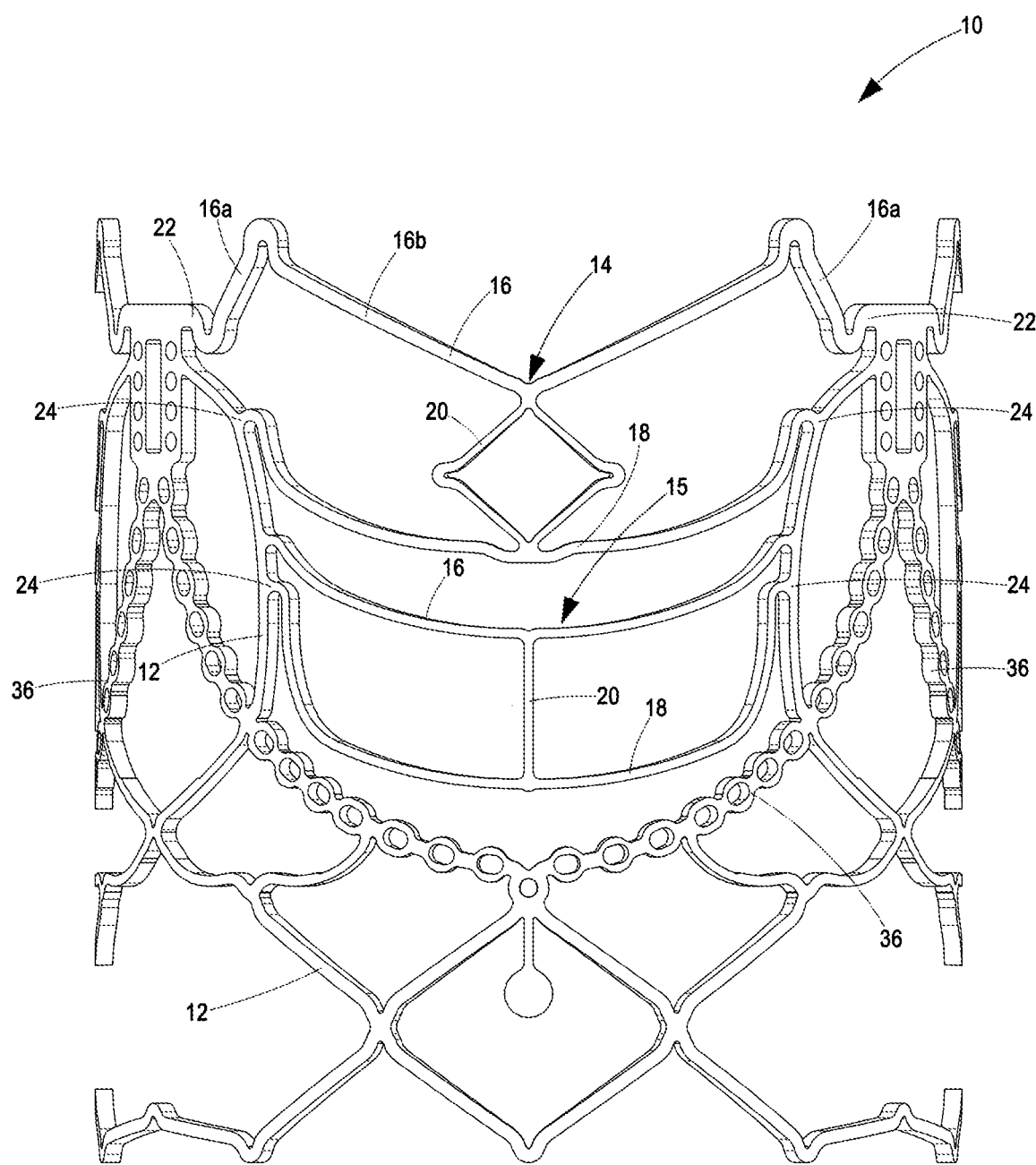
FIG. 2 is a side view of the stent in FIG. 1.

With reference to FIGS. 1 to 6 of the drawings, an expandable cylindrical stent 10 is formed by laser cutting a single right circular cylindrical tube to form lattice members 12, first arms 14 and second arms 15. The lattice members 12 and arms 14 and 15 form an integral part of the cylindrical wall of the stent 10, which is typically between 18 mm and 30 mm in outer diameter.

The lattice members 12 form a lattice, in the sense that they are connected to each other at junctions, which formation permits the stent 10 to be crimped (i.e. radially compressed) under the influence of an enveloping external radially compressive force. The lattice members 12 need not necessarily form a regular diamond-shaped structure. For a 23 mm outer diameter stent 10 (which is typically made from a 23 mm outer diameter tube), the lattice member width may vary between 100 μm and 1000 μm, but is most preferably between 200 μm and 600 μm.

The stent 10 may be made of stainless steel, cobalt-chromium alloys such as L605 and MP35N, or tantalum alloys. Accordingly, the stent 10 is plastically deformable from an initial condition shown in FIGS. 1 and 2 to a fully crimped condition shown in FIG. 3, to a pinched condition shown in FIG. 4, and to a radially expanded condition shown in FIGS. 5 and 6.

Each of the first and second arms 14 and 15 comprises a first non-linear member 16, a second non-linear member 18 and a bridge member 20. In this regard, it should be appreciated that adjacent, axially-spaced U-shaped members without a bridge extending therebetween should not be regarded as an "arm".

The first arm 14 is disposed at a second axial end of the stent 10, and the second arm 15 is axially aligned with and spaced from the first arm 14 towards the first axial end of the stent 10. It will be appreciated that the term "axially aligned" does not require the first and second arms 14 and 15 to be disposed on the stent axis A-A. "Axially aligned" is intended to be interpreted to mean that the first and second arms 14 and 15 are disposed on a line that runs parallel to the stent axis A-A.

Referring specifically to the first arm 14: The first member 16 is generally M-shaped, defining a pair of leg portions 16a with a central portion (typically curved or U-shaped) 16b therebetween. It will be appreciated that although the central portion 16b has been shown as U-shaped, this central portion 16b could be straight. The first member 16 is also of variable stiffness along its length—the axial ends of the first member 16 (i.e. the leg portions 16a) defining stiffened portions that are spaced from each other to define a deformable portion there between (i.e. the curved central portion 16b). The stiffened portions 16a could be thicker than the deformable curved central portion 16b. For instance, the stiffened portions 16a could be 1.5 to 3 times the width of the deformable curved central portion 16b/the lattice members 12. Alternatively, the stiffened portions 16a could be treated (e.g. heat treated) to increase the shore hardness of the first member 16 in these regions. The stiffened portions 16a are typically stiffer (i.e. more resistant to deformation) than any other portion of the first member 16, second member 18, bridge member 20 and lattice members 12.

Preferably, each stiffened portion 16a of the first member 16 of the first arms 14 is at least 1.3 mm in length and at most 2.3 mm in length.

The first member 16 of the first arm 14 is connected at its axial ends to lattice members 12 at respective first junctions 22.

Referring specifically to the second arm 15: The first member 16 is generally U-shaped and is of uniform stiffness along its length.

The circumferential spacing between the axial ends of the first member 16 of each first arm 14 is greater than the circumferential spacing between the axial ends of the first member 16 of each second arm 15.

Importantly, in respect of both the first and second arms 14 and 15, the first member 16 is non-linear so as to permit the first member 16 to straighten when subject to a tensile axial force.

Importantly, in respect of both the first and second arms 14 and 15, the first member 16 is not connected to lattice members 12 otherwise than at the axial ends of the first member 16. This ensures that the first member 16 is free from restraint induced by lattice members 12 other than at the axial ends of the first member 16.

In respect of each of the first and second arms 14 and 15: the second non-linear member 18 is generally U-shaped and typically of uniform stiffness along its length. Importantly, the second member 18 is non-linear so as to permit the second member 18 to straighten when subject to a tensile axial force. The second member 18 is connected at its axial ends to lattice members 12 at respective second junctions 24 and extends from its axial ends towards: (i) a first axial end of the stent 10; and (ii) towards the bridge 20. Importantly, the second member 18 is not connected to lattice members 12 otherwise than at the axial ends of the second member 18. This ensures that the second member 18 is free from restraint induced by lattice members 12 other than at the axial ends of the second member 18.

It will be appreciated that the second members 18 of each of the first and second arms 14 and 15 extend in the same direction. This should be contrasted against the stent described in WO2011/002996, which shows opposed axially spaced and aligned arms (i.e. where the arms extend in opposite directions).

The circumferential spacing between the axial ends of the second member 18 of the first arm 14 is greater than the circumferential spacing between the axial ends of the second member 18 of the second arm 15. Furthermore, in respect of each second arm 15, the axial ends of the first member 16 of the second arm 15 are spaced from the axial ends of the second member 18 of the second arm 15, with at least a portion of a lattice member 12 extending therebetween.

Figure 7:
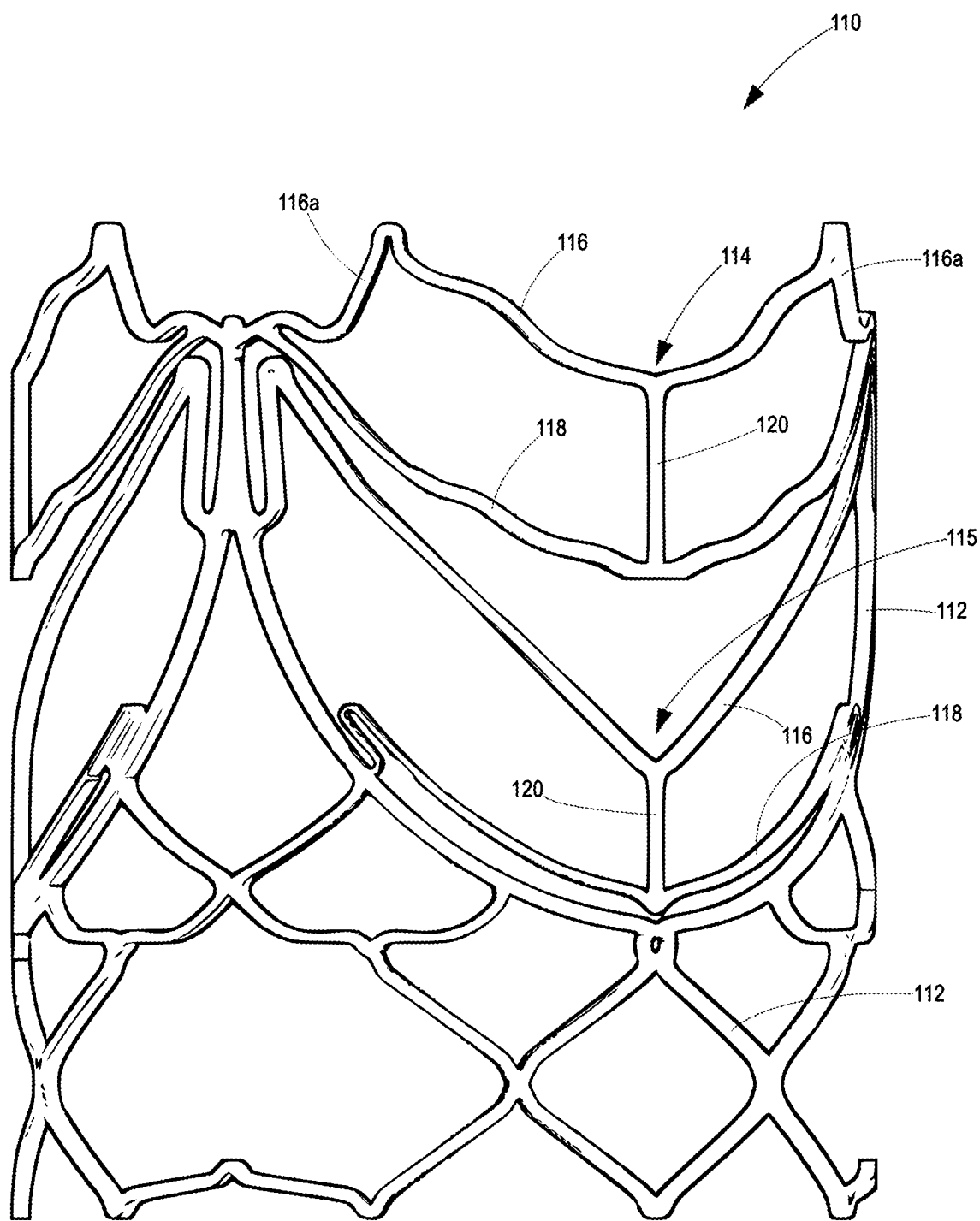
FIG. 7 is a side view of an expandable cylindrical stent according to a first alternative embodiment of a first aspect of the invention.
Figure 8:
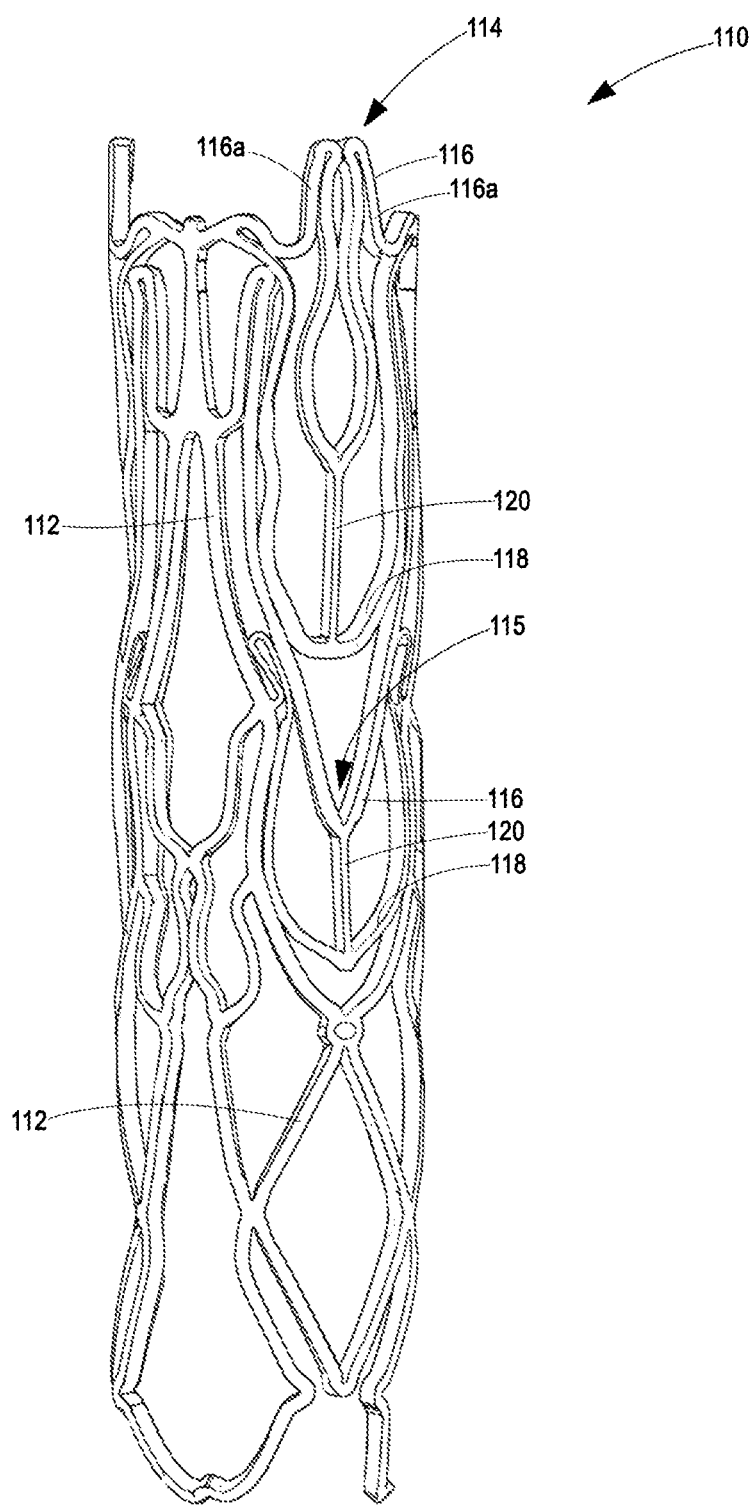
FIG. 8 is a side view of the stent in FIG. 7 in a fully crimped condition.
Figure 9:
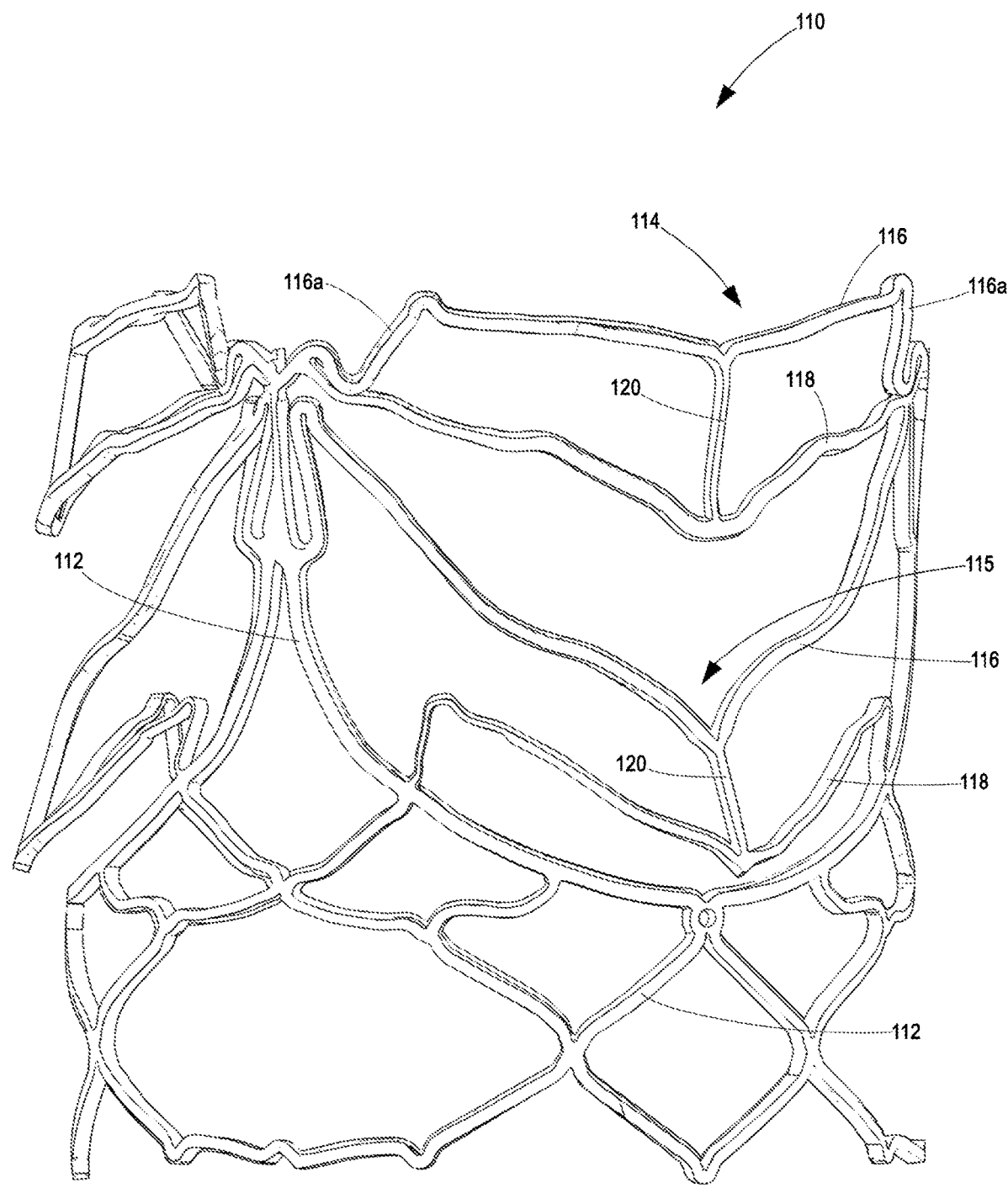
FIG. 9 is a side view of the stent in FIG. 7 in a radially expanded condition.

In respect of the first arm 14, FIGS. 1 to 6 show the first and second junctions 22 and 24 being spaced from each other. However, (as shown in FIGS. 7 to 9), the first junctions could be coincident with the second junctions.

In respect of each of the first and second arms 14 and 15, the second member 18 is less than 28 mm in length, more preferably, less than 20 mm in length and even more preferably less than 16 mm in length. Accordingly, the second member 18 protrudes from the second junctions 24 less than 14 mm (i.e. half its longest length of 28 mm) (see FIG. 2). By "length", the actual length is meant, i.e. the length of the second member, whether in its non-linear form or whether it were straightened.

Optionally, the length of the first member 16 of the first arm 14 is longer than the length of the first member 16 of the second arm 15. Further optionally, the length of the second member 18 of the first arm 14 is longer than the length of the second member 18 of the second arm 15.

Turning specifically to the first arm 14, the stiffened portions 16a of the first member 16 on the one hand and the second member 18 on the other hand are disposed on opposite sides of a virtual plane 26 shown in FIG. 1 that: (i) extends between the respective first junctions 22; and (b) is transverse the longitudinal axis A-A of the cylindrical stent 10.

In respect of each of the first and second arms 14 and 15, a bridge member 20 extends between the first member 16 and the second member 18, so as, during crimping and radial expansion of the stent 10, to transfer forces between the first and second members 16 and 18. Although FIGS. 1 to 6 show a single bridge member 20 spanning the first and second members 16 and 18, each of the arms 14 and 15 could include any number of bridge members 20. FIGS. 1 to 6 do not show bridge members 20 connected directly to lattice members 12. However the bridge members 20 may connect to lattice members 12 at the first and second junctions 22 and 24.

FIGS. 1 to 6 shows stents 10 with: three first arms 14 that are circumferentially equi-offset relative to each other; and three second arms 15 that are circumferentially equi-offset relative to each other.

Figure 6:
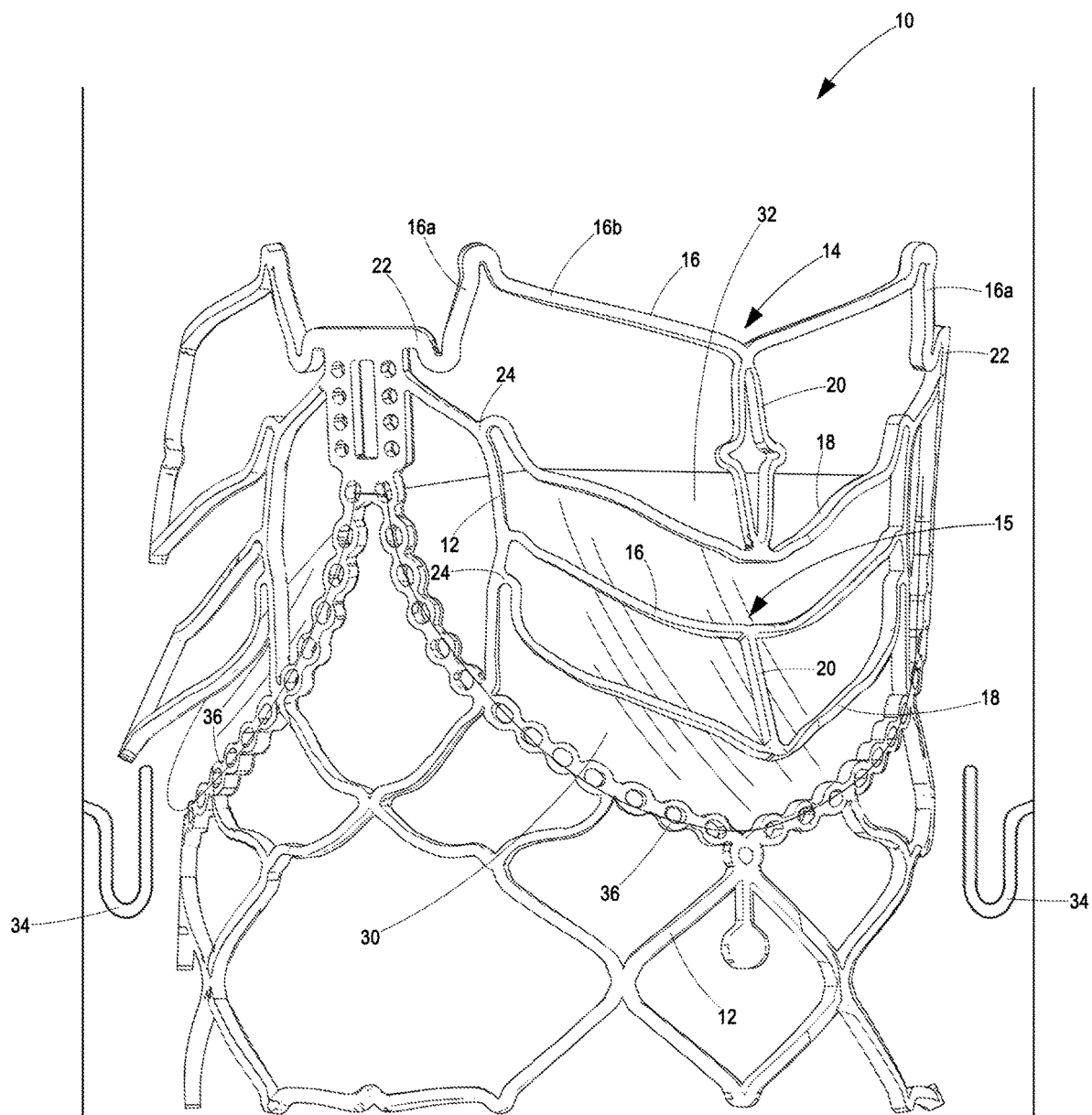
FIG. 6 is a side view of the stent in FIG. 1 in a radially expanded condition, with the stent located within an aortic root.

Turning specifically to FIG. 6, valve 30 leaflets 32 (e.g. a tri-leaflet polymer or tissue valve with a thickness varying between 50 μm and 500 μm) could be located within the stent 10; and (ii) secured to an arcuate-shaped lattice members 36. The stent 10 shows three contiguous arcuate-shaped lattice members 36 that extend continuously around the perimeter of the stent 10. By "contiguous", it is meant that each arcuate-shaped lattice member 36 terminates side-by-side with its adjacent arcuate-shaped lattice member 36 to form a continuous series of arcuate-shaped lattice members 36 that extend around the perimeter of the stent 10. Further, the arcuate-shaped lattice members 36 are formed integrally with the stent 10 and each other. Each arcuate-shaped lattice member 36 also defines a series of apertures or rings to facilitate suturing of valve 30 leaflets 32 to the stent 10 (via such apertures or rings). The addition of the valve 30 enables the stent 10 to act as a replacement valve.

Although each arcuate-shaped lattice member 36 is shown as being axially aligned with the first and second arms 14 and 15, it will be appreciated that each arcuate-shaped lattice member 36 need only extend along at least 25% of the perimeter of the stent.

FIGS. 7 to 9 show an alternative embodiment of the expandable cylindrical stent 110. This alternative embodiment similarly includes lattice members 112, three first arms 114 and three second arms 115, with each of the first and second arms 114 and 115 including first and second members 116 and 118 and a bridge 120 extending between such first and second members 116 and 118.

FIGS. 7 to 9 show the absence of lattice members 112 extending axially between adjacent stiffened portions 116a of adjacent first members 116 of adjacent first arms 114. This enables such adjacent stiffened portions 116a of adjacent first members 116 of adjacent first arms 114 to deform towards each other during crimping without intervening lattice members (or portions of the second member 118 on the first arm 114) inhibiting such deformation. The ability to deform freely towards each other, so as to permit contact between such adjacent stiffened portions 116a of adjacent first members 116 of adjacent first arms 114, enables the stent 110 to be crimped more effectively than the stent described in WO2011/002996. In contrast, the stent described in WO2011/002996 described the first member (including stiffened portions thereof) and the second member (including stiffened portions thereof) disposed on the same side of a virtual plane that: (i) extends between the junction of the first member and lattice members; and (ii) is transverse the longitudinal axis of the stent. Accordingly, during compression of the stent described in WO2011/002996, the presence of lattice members and the second member between adjacent stiffened portions of adjacent first members, restricts deformation of such adjacent stiffened portions during crimping.

Figure 10:
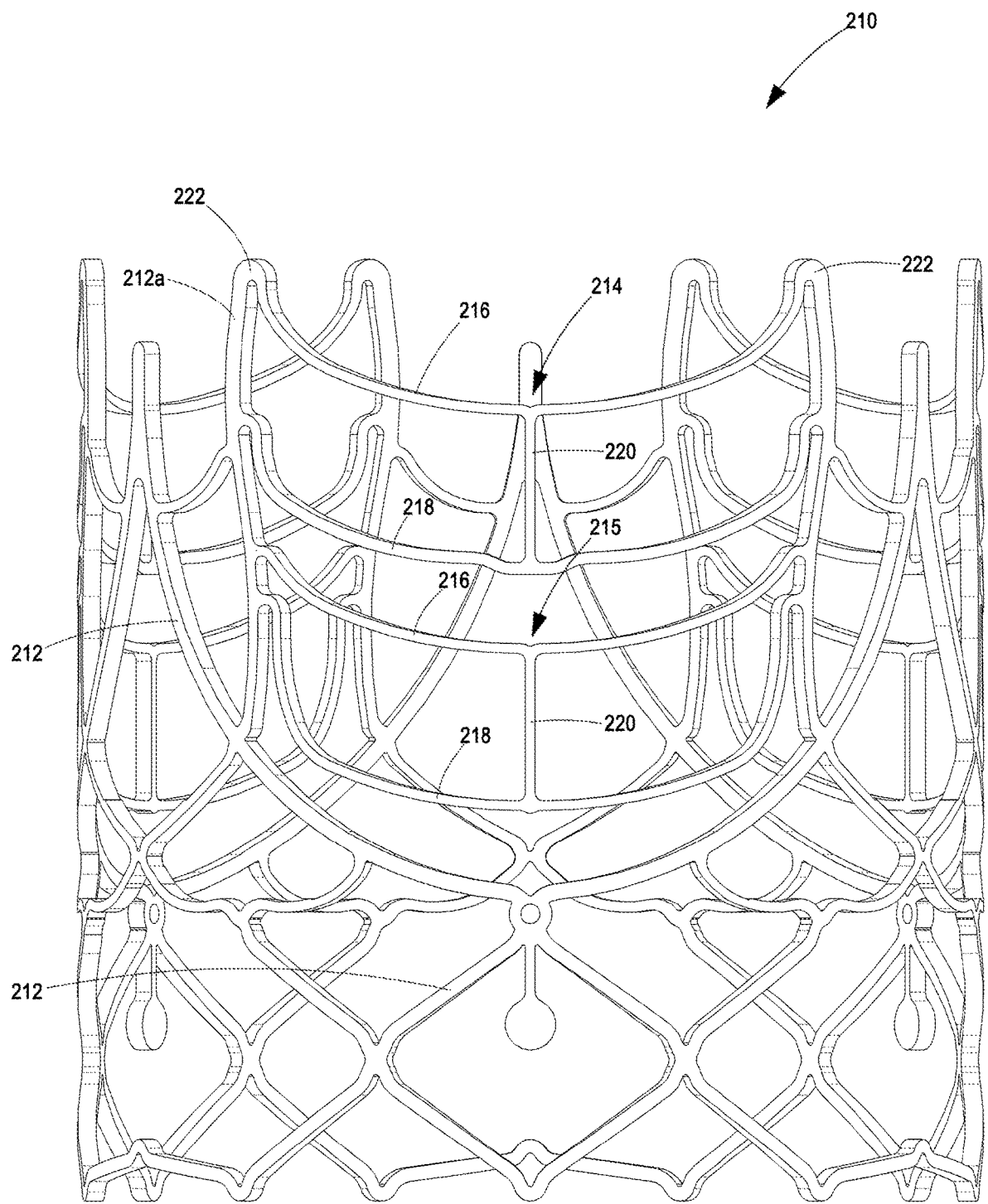
FIG. 10 is a side view of an expandable cylindrical stent according to a second alternative embodiment of a first aspect of the invention.

FIG. 10 shows a second alternative embodiment of the expandable cylindrical stent 210. This second alternative embodiment similarly includes lattice members 212 (which includes a post 212a), three first arms 214 and three second arms 215, with each of the first and second arms 214 and 215 including first and second members 216 and 218 and a bridge 220 extending between such first and second members 216 and 218. The first member 216 of the first arm 214 is connected to the lattice member 212 (in the form of the lattice post 212a) at junctions 222.

According to a second aspect of the invention (and with reference to the preferred embodiment of the stent 10), a method of crimping an expandable cylindrical stent 10 includes the steps of:

Placing a stent 10 in its initial condition (i.e. not deformed from its original tubular shape) into a crimping device (not shown) for applying an enveloping radial compressive force to the stent 10.

Crimping the stent 10, thereby causing primary deformation of the lattice members 12 that induces: (i) relative angular displacement of the lattice members 12 at their junctions (i.e. points of connection to each other) and general deformation of lattice members 12 to a collapsed state; and (ii) adjacent first members 16 of adjacent first arms 14 towards each other. In an embodiment now shown, such adjacent first members 16 of adjacent first arms 14 could contact each other during such crimping process. It will be appreciated that, since the stiffened portions 16a of the first member 16 of the first arm 14 are more resistant to deformation than that other members 12, 18 and 20 forming the stent 10, the stiffened portions 16a of the first member 16 of the first arm 14 undergo less deformation than such other members 12, 18 and 20.

Figure 3:
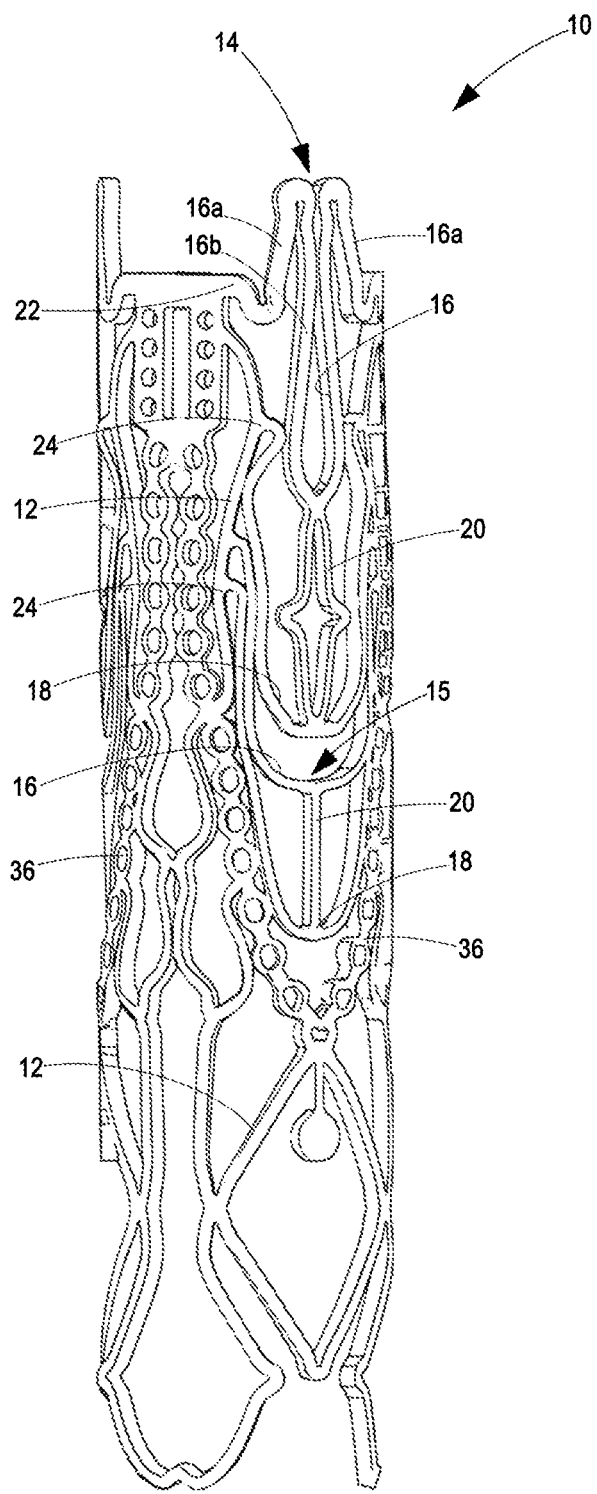
FIG. 3 is a side view of the stent in FIG. 1 in a fully crimped condition.

With the lattice members 12 fully (or near-fully) compressed and no lattice members extending axially between adjacent first members 16 of adjacent first arms 14, further compression (i.e. additional radial compressive force) causes the stiffened portions 16a of the first members 16 of the first arms 14 plastically further to deform. This fully crimped condition is shown in FIG. 3. When in the fully crimped condition, the stent 10 outer diameter is reduced to less than 10 mm, preferably less than 6 mm. It will be appreciated that the crimping device must be capable of applying: a first degree of radial compressive force to cause the stent 10 to deform to the partially crimped condition; and a second degree of radial compressive force (which is higher than the first degree of radial compressive force) to cause the stent to deform to the fully crimped condition.

Figure 4:
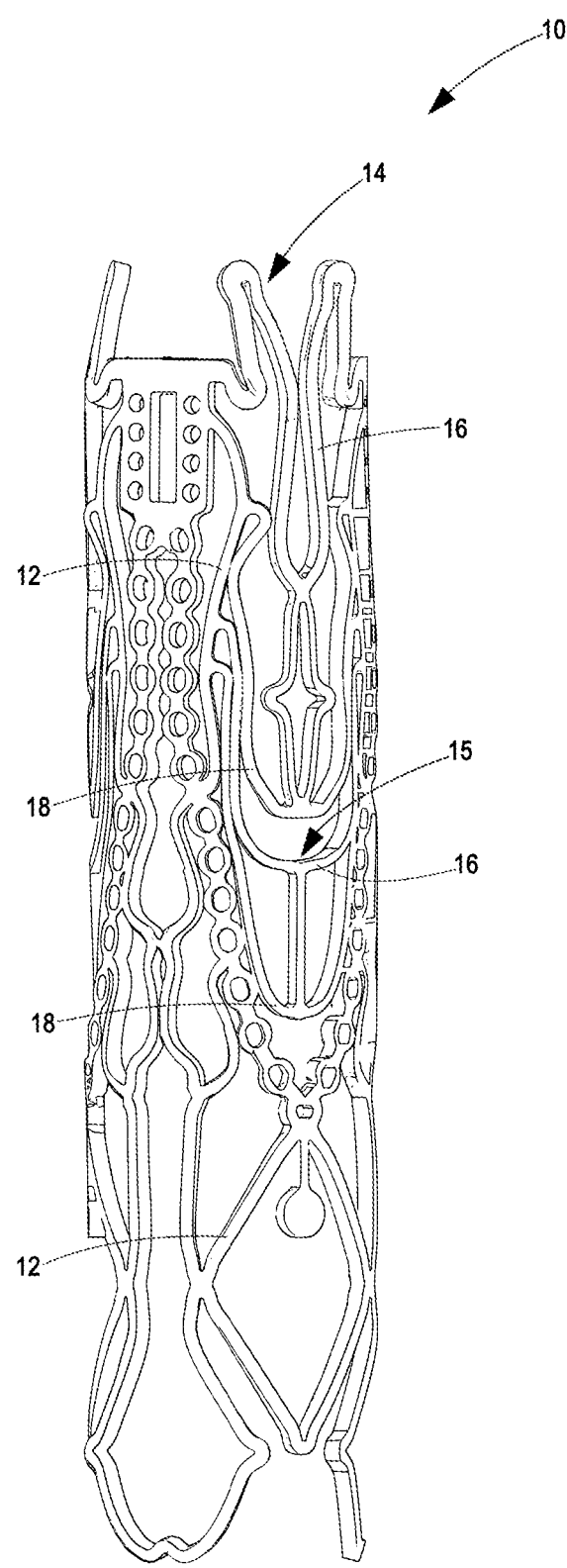
FIG. 4 is a side view of the stent in FIG. 1 in a pinched condition.
Figure 5:
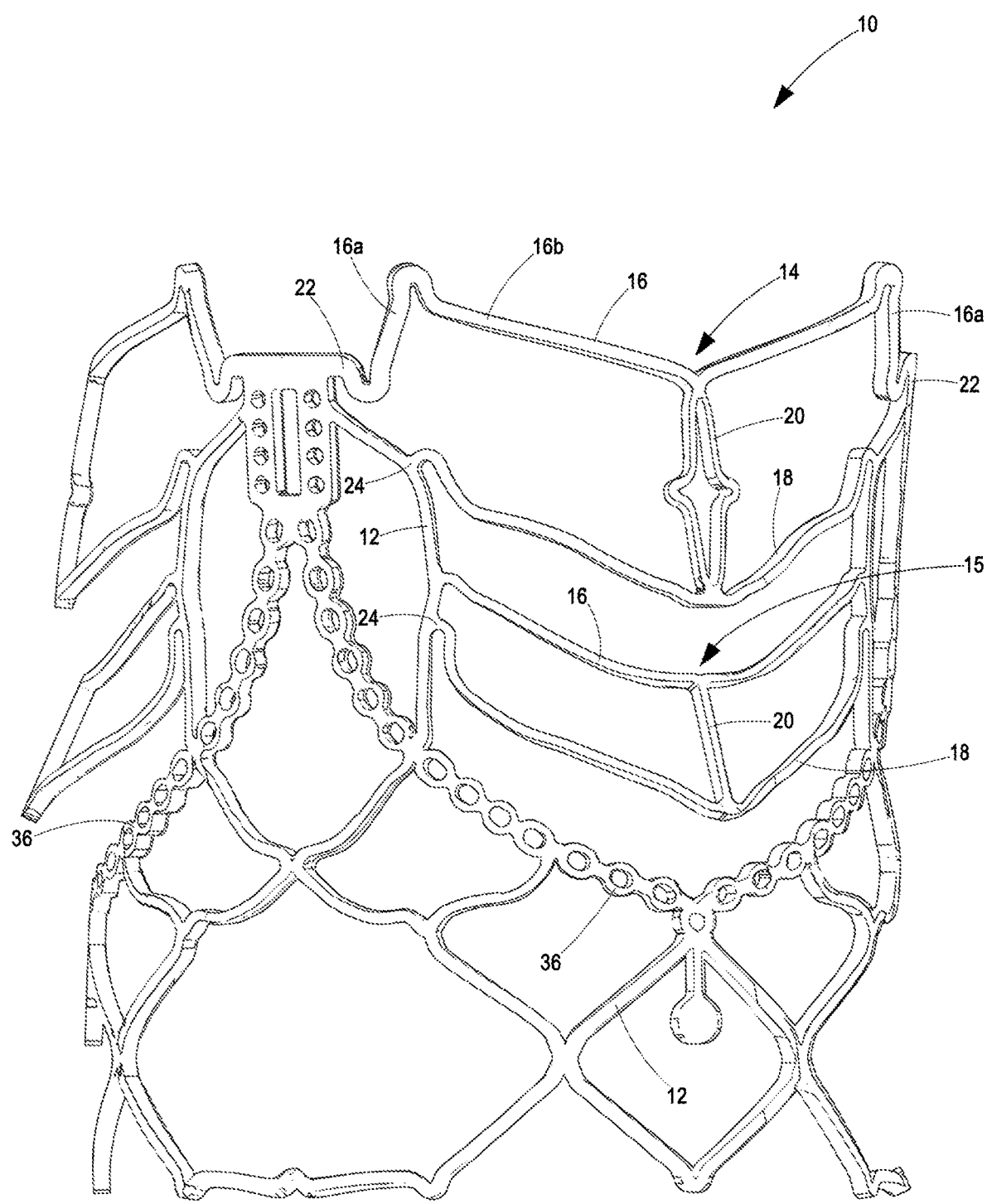
FIG. 5 is a side view of the stent in FIG. 1 in a radially expanded condition.

In the fully crimped condition, the stiffened portions 16a of adjacent first member 16 or adjacent first arms 14 may be pinched towards each other. For this purpose, a pinching tool (not shown) may be applied to such adjacent stiffened portions 16a of adjacent first members 16 of adjacent first arms further plastically to deform them towards each other. This pinched condition is shown in FIG. 4.

Turning to FIG. 6, according to a third aspect of the invention (and with reference to the preferred embodiment of the stent 10), a method of radially expanding an expandable cylindrical stent 10 includes the steps of:

Inserting a stent 10 that has been crimped (and optionally pinched into the pinched condition) into an vessel (e.g. an aorta).

Locating the stent 10 through a valve 34 (e.g. a mitral valve) with the first and second arms 14 and 15 extending beyond the valve 34 cusps/leaflets.

Radially expanding the stent 10 from the crimped (or, optionally, pinched) condition by radially expanding a dilatation device (not shown) disposed axially within the stent 10. The dilatation device could, for example, be a mechanical expander, an inflatable cylindrical balloon or an inflatable spiral.

The dilatation device is capable of applying sufficient force to cause the lattice elements 12 to deform to their initial condition shown in FIG. 1. However, the dilatation device does not apply sufficient force to cause the stiffened portions 16a of the first members 16 of the first arms 14 to deform to their initial condition shown in FIG. 1. Since the stiffened portions 16a resist rotation back to their initial condition, the non-linear first member 16 of the first arms 14 must straighten to enable the diameter of the stent 10 in the vicinity of the first members 16 of the first arms 14 radially to expand to its initial diameter shown in FIG. 1.

Straightening of the first members 16 of the first arms 14 induces tension in the bridge member 20 of the first arms 14, which tension induces the second members 18 of the first arms 14 to protrude radially outwards relative to the adjacent lattice members 12. It will be appreciated that: (i) the configuration of the stent 10; and (ii) the presence of the dilatation device within the stent 10, prevents the second members 18 of the first arms 14 from protruding radially inwards. Similarly, expansion of the stent 10 causes the second member 18 of the second arms 15 to protrude radially outwards relative to the adjacent lattice members 12. When expanded, the second arms 15 protrude radially outwards relative to the adjacent lattice members 12 to a greater degree than the first arms 14, Prior to the stent 10 being fully expanded, the stent 10 is moved towards the free ends of the valve 34 leaflets. Further radial expansion of the stent 10 causes: the stent 10 to bear against the aorta/valve 34; the first members 16 of the first arms 14 and second arms 15 to straighten further; and the first and second arms 14 and 14 further to protrude radially.

Since: (i) the second members 18 of the first and second arms 14 and 15 are less than 28 mm in length and protrude less than 14 mm (see FIG. 2) from the axial ends of their first members 16; and (ii) the valve 34 leaflets are typically 14 mm in length (i.e. from their connection with the aorta wall to their free end), it will be appreciated that the first and second arms 14 and 15 do not extend to the intersection between the valve 34 and the aorta wall. Instead, one of the first and second arms 14 and 15 may rest on the free ends of the valve 34 leaflets.

In use, the first and second arms 14 and 15 prevent embolization or migration of the stent 10 as a result of forward blood flow and the back blood pressure.

It will be appreciated that since:
- the first member 16 of the first arm 14 is not connected to lattice members 12 otherwise than at the axial ends of such first member 16 (i.e. such first member 16 is free from restraint induced by lattice members 12 other than at the axial ends of such first member 16); and
- the stiffened portions 16a of the first member 16 of the first arm 14 on the one hand and the second member 18 of the first arm 14 on the other hand are disposed on opposite sides of the virtual plane 26, upon radial expansion of the stent 10 from a crimped or pinched condition under the influence of an external force (i.e. induced by the dilatation device) consequential tension in the lattice members 12 at the first junctions 22 (i.e. at a first axial end of the stiffened portions 16a of the first member 16 of a first arm 14) coupled with consequential tension in the first member 16 of the first arm 14 (i.e. at a second axial ends of the stiffened portions 16a) causes rotation of the stiffened portions 16a of the first member 16 of the first arm 14 at the first junctions 22, thereby causing the ends of the stiffened portions 16a distal the second member 18 of the first arm 14 to rotate towards each other. In other words, such rotation causes the stiffened portions 16a of adjacent first member 16 of adjacent first arms 14 to diverge.

The length of a stiffened portion 16a of the first member 16 of a first arm 14 influences the degree of protrusion of the second member 18 of the first arm 14 upon radial expansion of the stent 10.

It will be appreciated that:
- Whereas the stent described in WO00/64355 includes barbs that protrude radially even when in the radially crimped condition, the stent 10 according to the present invention includes first and second arms 14 and 15 that do not protrude radially outwards from the stent 10 cylindrical wall when in the fully crimped condition.
- Whereas the stents described in GB2513195 and U.S. Pat. No. 8,992,608 require a customised dilatation device that not only radially expands the stent but also causes radial extension of the arms, the stent 10 according to the present invention requires a dilatation device that merely radially expands the stent 10—the configuration of the stent 10 causes radially protrusion of the first and second arms 14 and 15 upon radial expansion of the stent 10.
- Whereas U.S. Pat. No. 8,992,608 requires axial compression of the stent to cause arms to protrude radially, the stent 10 according to the present invention causes radial protrusion of the first and second arms 14 and 15 upon radial expansion of the stent 10 alone.
- Whereas U.S. Pat. No. 8,216,301 describes arms that do not form part of the cylindrical wall of the stent and must be restrained prior to being deployed radially outwards, the first and second arms 14 and 15 according to the present invention form an integral part of the stent 10 cylindrical wall and do not require any restraint to prior to radial expansion of the stent 10 from the pinched/fully crimped condition.
- WO2011/002996 describes a stent including opposed axially spaced arms (i.e. axially spaced and aligned arms that extend towards each other), whereas the stent 10 according to the present invention includes axially spaced and aligned first and second arms 14 and 15 that extend in the same direction (i.e. towards the same axial end of the stent 10). With its first and second arms 14 and 15 axially aligned, should the stent 10 according to the present invention shift axially along a vessel, such that a second arm 15 passes (for example) a valve leaflet free edge, the corresponding first arm 14 of the stent 10 has an opportunity to engage with and rest on the same valve leaflet free edge and thereby anchor the stent in the vessel. Furthermore, WO2011/002996 describes a stent wherein adjacent stiffened portions of adjacent arms are connected to each other at or near a point on the stiffened portions that are distal the second member. Accordingly, upon radial expansion of the stent, these stiffened portions diverge from this point on the stiffened portions. Such divergence permits deformation of the second member and not deformation (i.e. extension) of the first member during radial expansion of the stent. Whereas, the stent 10 according to the present invention includes stiffened portions 16a on first members 16 of first arms 14 that are connected to lattice members 12 at a point on the stiffened portions 16a proximal the second member 18. Accordingly, upon radial expansion of the stent 10, these stiffened portions 16a diverge from this point on the stiffened portions 16a. Such divergence permits deformation of the deformable curved central portion 16b of the first member 16 and not (directly) deformation of the second member 18 during radial expansion of the stent 10—deformation of the second member 18 of the first arm 14 is caused by tension in the bridge member 20 induced by straightening of the first member 16 of the first arm 14.

The invention claimed is:

1. An expandable stent comprising a cylindrical wall made up of:
   - lattice members connected to each other;
   - at least one first arm that comprises:
     - a first non-linear member that is connected at each of its axial ends to a lattice member at respective first junctions; and
     - a second non-linear member connected at each axial end to:
       - (i) a lattice member; or
       - (ii) the first non-linear member of the first arm,
     - which connections restrain the axial ends of the first arm's second non-linear member from protruding from the surrounding stent wall during:
     - radial expansion of the stent, and consequent protrusion of the first arm radially outwards from the surrounding stent wall; and
     - at least one bridge member extending between the first non-linear member and the second non-linear member,
   - at least one second arm that comprises:
     - a first non-linear member that is connected at each of its axial ends to a lattice member; and
     - a second non-linear member connected at each axial end to a lattice member, which connections restrain the axial ends of the second arm's second non-linear member from protruding from the surrounding stent wall during: radial expansion of the stent, and consequent protrusion of the second arm radially outwards from the surrounding stent wall; and
     - at least one bridge member extending between the first non-linear member and the second non-linear member,
   - characterised in that:
   - the second non-linear member of the first arm is generally U-shaped, extending from its axial ends towards: (i) a first axial end of the stent; and (ii) towards the bridge of the first arm;
   - the second non-linear member of the second arm is generally U-shaped, extending from its axial ends towards: (i) a first axial end of the stent; and (ii) towards the bridge of the second arm;

the first arm is disposed at a second axial end of the stent, and the second arm is:
(i) axially spaced from the first arm towards the first axial end of the stent; and (ii) axially aligned with the first arm;

the first non-linear member of each of the first and second arms is connected to lattice members at the first non-linear member's axial ends only;

the second non-linear member of the first arm is connected to: (i) lattice members;

or (ii) the first non-linear member of the first arm, at the first arm's second non-linear member's axial ends only; and the second non-linear member of the second arm is connected to lattice members at the second arm's second non-linear member's axial ends only, such that, upon radial expansion of the stent from a radially crimped condition under the influence of an external force, tension in: (i) the bridge of the first arm; and (ii) the bridge member of the second arm, causes the second non-linear members of both the first and second arms to protrude from the first and second arms' second non-linear members' connected axial ends radially outwards from the surrounding stent wall, respectively.

2. A stent according to claim 1, wherein the length of the first non-linear member of the first arm is longer than the length of the first non-linear member of the second arm.

3. A stent according to claim 2, wherein the circumferential spacing between the axial ends of the second non-linear member of the first arm is greater than the circumferential spacing between the axial ends of the second non-linear member of the second arm.

4. A stent according to claim 3, wherein the first non-linear member of the first arm defines a stiffened portion at each axial end of such first non-linear member, which stiffened portions are spaced from each other to define a deformable portion therebetween.

5. A stent according to claim 4, wherein the first non-linear member of the first arm is substantially M-shaped, defining a pair of leg portions with a curved portion therebetween, wherein each leg portion comprises a stiffened portion and the curved portion comprises the deformable portion.

6. A stent according to claim 5 including: (i) three first arms that are circumferentially equi-offset from each other; and (ii) three second arms that are circumferentially equi-offset from each other.

7. A stent according to claim 6, wherein, in respect of each second arm, the axial ends of the first non-linear member of the second arm are spaced from the axial ends of the second non-linear member of the second arm, with at least a portion of a lattice member extending therebetween.

8. A stent according to claim 7, wherein the circumferential spacing between the axial ends of the first non-linear member of each first arm is greater than the circumferential spacing between the axial ends of the first non-linear member of each second arm.

9. A stent according to claim 8, wherein the first non-linear member of each second arm is generally U-shaped.

10. A stent according to claim 9, wherein, in respect of each first arm:

each stiffened portion of the first non-linear member of the first arm is at least 1.3 mm in length; and the stiffened portions of the first non-linear member of the first arm on the one hand and the second non-linear member of the first arm on the other hand are disposed on opposite sides of a virtual plane that: (i) extends between the respective first junctions; and (ii) is transverse the longitudinal axis of the stent, such that, upon radial expansion of the stent from a radially crimped condition under the influence of an external force, tension in the lattice members at the first junctions causes rotation of the stiffened portions of the first non-linear member of the first arm at the first junctions, thereby causing the ends of the stiffened portions distal the second non-linear member of the first arm to rotate towards each other.

11. A stent according to claim 10, wherein the stent is right circular cylindrical in shape.

12. A stent according to claim 11, further including valve leaflets: (i) located within the stent; and (ii) secured to lattice members.

13. A stent according to claim 12, wherein: (i) three contiguous lattice members are arcuate in shape; (ii) each arcuate-shaped lattice member extends along at least 25% of the perimeter of the stent; (iii) each arcuate-shaped lattice member defines a series of apertures or rings along its length; and (iv) the valve leaflets are sutured to such 35 arcuate shaped lattice members via such apertures or rings.

14. A method of crimping a stent according to claim 6, which method includes the steps of:

causing primary deformation of the lattice members that induces: (i) relative angular displacement of the lattice members at their points of connection to 5 each other and general deformation of lattice members to a collapsed state; and (ii) adjacent first non-linear members of adjacent first arms to contact each other; and causing secondary deformation of the lattice members wherein further compression of the collapsed lattice members causes the stiffened portions of the first non-linear members of each first arm plastically to deform.

15. A method of crimping a stent according to claim 14, further including the step of pinching adjacent stiffened portions of adjacent first non-linear members of adjacent first arms together, thereby causing such stiffened portions further to deform plastically.

16. A method of expanding a stent according to claim 6, which method includes the steps of:

positioning the stent that has previously been crimped through a heart valve 20 with the first arms and the second arms extending past the free ends of the valve leaflets;

expanding a dilatation device within the stent to cause: (i) the stent to expand; and (ii) the first and second arms to protrude radially relative to the adjacent 25 lattice members; and displacing the stent axially relative to the valve to cause the first arms or the second arms to rest on the free ends of the valve leaflets, with the free ends of the resting first arms or second arms spaced from the intersection of the valve 30 leaflets and aortic root.

* * * * *

UNITED STATES PATENT AND TRADEMARK OFFICE
CERTIFICATE OF CORRECTION

| | |
|---|---|
| PATENT NO. | : 10,792,149 B2 |
| APPLICATION NO. | : 16/086480 |
| DATED | : October 6, 2020 |
| INVENTOR(S) | : Grant Leigh Nelson et al. |

It is certified that error appears in the above-identified patent and that said Letters Patent is hereby corrected as shown below:

In the Specification

Column 4, Line 13, "and (H) axially aligned with the first arm; and" should read -- and (ii) axially aligned with the first arm; and --.

Signed and Sealed this
Seventeenth Day of November, 2020

Andrei Iancu
*Director of the United States Patent and Trademark Office*